US009550293B2

(12) United States Patent
Hatakeyama

(10) Patent No.: US 9,550,293 B2
(45) Date of Patent: Jan. 24, 2017

(54) MANIPULATOR

(71) Applicant: OLYMPUS CORPORATION, Tokyo (JP)

(72) Inventor: Naoya Hatakeyama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/842,115

(22) Filed: Sep. 1, 2015

(65) Prior Publication Data

US 2015/0367508 A1    Dec. 24, 2015

Related U.S. Application Data

(63) Continuation of application No. PCT/JP2014/050296, filed on Jan. 10, 2014.
(Continued)

(51) Int. Cl.
*B25J 17/00* (2006.01)
*B25J 9/06* (2006.01)
(Continued)

(52) U.S. Cl.
CPC .............. *B25J 9/06* (2013.01); *A61B 34/30* (2016.02); *A61B 34/71* (2016.02); *A61B 34/74* (2016.02);
(Continued)

(58) Field of Classification Search
CPC ........ B25J 9/104; B25J 9/06; Y10T 74/18576; Y10T 74/20323
(Continued)

(56) References Cited

U.S. PATENT DOCUMENTS 5,647,554 A * 7/1997 Ikegami ............... B25J 19/0025
  191/12.2 A
7,331,436 B1 * 2/2008 Pack .................... B65H 75/425
  191/12.2 A
(Continued)

FOREIGN PATENT DOCUMENTS

EP    2349053        8/2011
EP    2529658 A1    12/2012
(Continued)

OTHER PUBLICATIONS

International Search Report dated Apr. 15, 2014 issued in PCT/JP2014/050296.
(Continued)

*Primary Examiner* — William Kelleher
*Assistant Examiner* — Zakaria Elahmadi
(74) *Attorney, Agent, or Firm* — Scully, Scott, Murphy & Presser, PC

(57) ABSTRACT

A manipulator includes an elongated main unit, a bending portion, and a distal end portion that are disposed in this order from a basal end; a plurality of main bending mechanisms having main linear members that extend from the distal end portion to the main unit, main motive-power generating portions), and main motive-power transmitting portions that transmit motive powers generated by the main motive-power generating portions to the main linear members in the form of linear motions in the longitudinal direction; a plurality of auxiliary bending mechanisms that are provided so as to form pairs with the respective main bending mechanisms and parallel thereto and that exert a pressing force and a tensile force on the distal end portion; and switching portions that selectively actuate either the main bending mechanisms or the auxiliary bending mechanisms, which are paired.

6 Claims, 17 Drawing Sheets

Related U.S. Application Data

(60) Provisional application No. 61/802,926, filed on Mar. 18, 2013.

(51) Int. Cl.
*B25J 9/10* (2006.01)
*A61B 17/00* (2006.01)

(52) U.S. Cl.
CPC ...... *B25J 9/104* (2013.01); *A61B 2017/00296* (2013.01); *A61B 2017/00314* (2013.01); *A61B 2017/00327* (2013.01); *A61B 2034/2055* (2016.02); *A61B 2034/306* (2016.02); *A61B 2034/715* (2016.02); *A61B 2090/0818* (2016.02); *Y10T 74/20323* (2015.01)

(58) Field of Classification Search
USPC .................. 74/89.23; 606/1, 130, 139, 205
See application file for complete search history.

(56) References Cited

U.S. PATENT DOCUMENTS

| | | | |
|---|---|---|---|
| 7,699,835 B2 * | 4/2010 | Lee | A61B 17/062 606/1 |
| 2003/0135204 A1 * | 7/2003 | Lee | A61B 90/36 606/1 |
| 2005/0107667 A1 * | 5/2005 | Danitz | A61B 1/0053 600/139 |
| 2006/0199999 A1 | 9/2006 | Ikeda et al. | |
| 2007/0142969 A1 | 6/2007 | Devengenzo et al. | |
| 2007/0283970 A1 | 12/2007 | Mohr et al. | |
| 2007/0287884 A1 | 12/2007 | Schena | |
| 2007/0287889 A1 | 12/2007 | Mohr | |
| 2007/0287992 A1 | 12/2007 | Diolaiti et al. | |
| 2008/0058861 A1 | 3/2008 | Cooper et al. | |
| 2008/0064921 A1 * | 3/2008 | Larkin | A61B 1/00087 600/104 |
| 2008/0064927 A1 | 3/2008 | Larkin et al. | |
| 2008/0064931 A1 | 3/2008 | Schena et al. | |
| 2008/0065097 A1 | 3/2008 | Duval et al. | |
| 2008/0065098 A1 | 3/2008 | Larkin | |
| 2008/0065099 A1 | 3/2008 | Cooper et al. | |
| 2008/0065100 A1 | 3/2008 | Larkin | |
| 2008/0065101 A1 | 3/2008 | Larkin | |
| 2008/0065102 A1 | 3/2008 | Cooper | |
| 2008/0065103 A1 | 3/2008 | Cooper et al. | |
| 2008/0065104 A1 | 3/2008 | Larkin et al. | |
| 2008/0065105 A1 | 3/2008 | Larkin et al. | |
| 2008/0065106 A1 | 3/2008 | Larkin | |
| 2008/0065107 A1 | 3/2008 | Larkin et al. | |
| 2008/0065108 A1 | 3/2008 | Diolaiti | |
| 2008/0065109 A1 | 3/2008 | Larkin | |
| 2008/0065110 A1 | 3/2008 | Duval et al. | |
| 2008/0071288 A1 | 3/2008 | Larkin et al. | |
| 2008/0071289 A1 | 3/2008 | Cooper et al. | |
| 2008/0071290 A1 | 3/2008 | Larkin et al. | |
| 2008/0071291 A1 | 3/2008 | Duval et al. | |
| 2009/0062814 A1 | 3/2009 | Omori et al. | |
| 2009/0112230 A1 * | 4/2009 | Jinno | B25J 9/104 606/130 |
| 2009/0326553 A1 | 12/2009 | Mustufa et al. | |
| 2009/0326556 A1 | 12/2009 | Diolaiti et al. | |
| 2010/0198232 A1 | 8/2010 | Diolaiti | |
| 2011/0071508 A1 | 3/2011 | Duval et al. | |
| 2011/0238081 A1 | 9/2011 | Cooper et al. | |
| 2011/0282351 A1 | 11/2011 | Cooper et al. | |
| 2011/0313428 A1 | 12/2011 | Mohr et al. | |
| 2012/0022553 A1 | 1/2012 | Cooper et al. | |
| 2012/0046669 A1 | 2/2012 | Duval et al. | |
| 2012/0065628 A1 * | 3/2012 | Naito | A61B 1/00078 606/1 |
| 2012/0083654 A1 | 4/2012 | Cooper et al. | |
| 2012/0203271 A1 | 8/2012 | Larkin et al. | |
| 2012/0209253 A1 * | 8/2012 | Donhowe | A61B 17/00 606/1 |
| 2012/0221011 A1 | 8/2012 | Larkin et al. | |
| 2013/0165908 A1 * | 6/2013 | Purdy | A61F 5/0013 606/1 |
| 2014/0094825 A1 * | 4/2014 | Flaherty | A61B 19/2203 606/130 |

FOREIGN PATENT DOCUMENTS

| | | |
|---|---|---|
| JP | H04-122592 A | 4/1992 |
| JP | 2001-353675 A | 12/2001 |
| JP | 2002-125919 A | 5/2002 |
| JP | 2006-061176 A | 3/2006 |
| JP | 2006061176 A * | 3/2006 |
| JP | 2009-539573 A | 11/2009 |
| JP | 2012-504017 A | 2/2012 |
| WO | WO 2007/146987 A2 | 12/2007 |
| WO | WO 2010/039394 A1 | 4/2010 |
| WO | 2011060311 A2 | 5/2011 |
| WO | WO 2011/145533 A1 | 11/2011 |

OTHER PUBLICATIONS

Extended Supplementary European Search Report dated Oct. 7, 2016 in related European Patent Application No. 14767539.1.

* cited by examiner

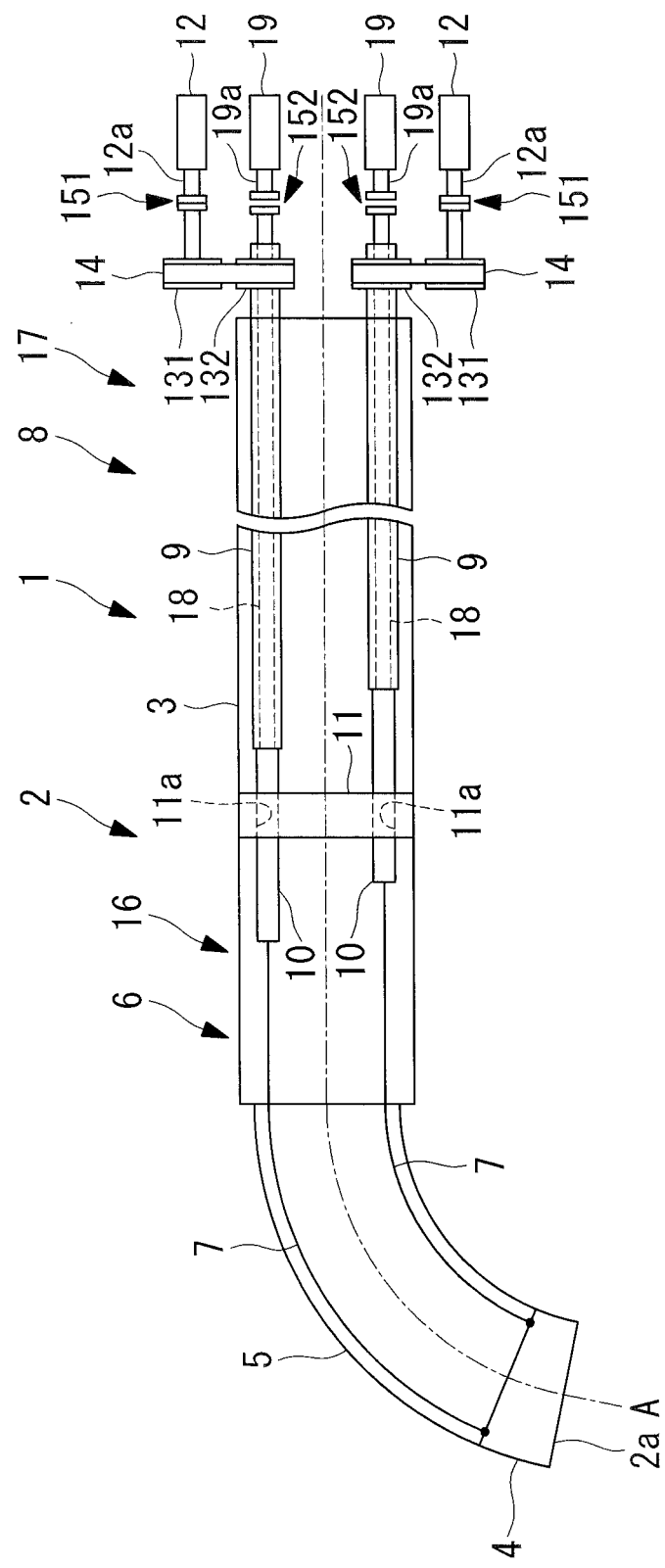

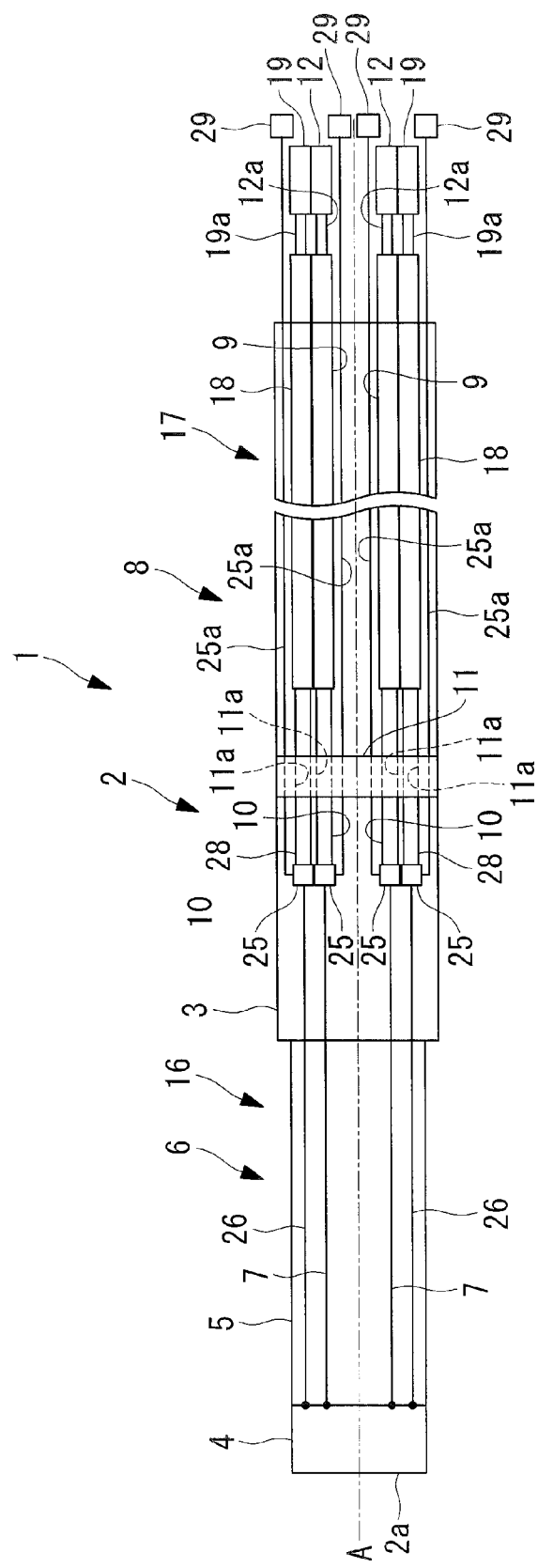

MANIPULATOR

CROSS-REFERENCE TO RELATED APPLICATIONS

This is a continuation of International Application PCT/JP2014/050296, with an international filing date of Jan. 10, 2014, which is hereby incorporated by reference herein in its entirety. This application claims the benefit of U.S. Provisional Patent Application No. 61/802,926, the content of which is incorporated herein by reference.

TECHNICAL FIELD

The present invention relates to a manipulator.

BACKGROUND ART

In the related art, there are known medical manipulators provided with an elongated inserted portion that can be inserted into a body for treating the body interior by remotely manipulating, from outside the body, a treatment tool installed in the inserted portion (for example, see Patent Literature 1). The inserted portion of such a manipulator is provided with a bending portion for changing the direction that a distal-end surface faces, in which a camera, a treatment tool, and so forth are installed.

In addition, in order to precisely control the bending angle of the bending portion, a gear mechanism is employed as a main bending mechanism for bending the bending portion. Specifically, the employed configuration is such that the bending portion is bent by converting a large rotational motion of a shaft generated at the basal end of the inserted portion to a small linear motion by means of a threaded shaft that rotates together with the shaft and a nut fastened to the threaded shaft, and by utilizing this linear motion to push and pull a wire connected to the distal end of the inserted portion.

In the inserted portion employing such a gear mechanism, in order to generate a rotational motion of the shaft from the linear motion of the wire, it is necessary to linearly move the wire with a sufficiently large external force. In other words, the shape of the bending portion bent by pushing and pulling the wire is sufficiently stable against an external force.

On the other hand, in order to switch to a state in which the bending portion is flexible and bent in accordance with the external force from a state in which the bending portion is rigid and the same angle is maintained against the external force, a clutch that is provided between the gear mechanism and the wire and that can separate them from each other is employed (for example, see Patent Literature 2).

CITATION LIST

Patent Literature

{PTL 1} Japanese Unexamined Patent Application, Publication No. 2006-61176
{PTL 2} Japanese Unexamined Patent Application, Publication No. 2002-125919

SUMMARY OF INVENTION

The present invention provides a manipulator including an elongated main unit; a distal end portion disposed at a distal end of the main unit; a bending portion that is provided between the main unit and the distal end portion and that is bendable; a plurality of main bending mechanisms that have main linear members that are connected to the distal end portion and that extend to the main unit by passing through the bending portion, main motive-power generating portions that generate motive powers, and main motive-power transmitting portions that are provided in the main unit and that transmit the motive powers generated by the main motive-power generating portions to basal ends of the main linear members in the form of a linear motion of the main unit in the longitudinal direction; a plurality of auxiliary bending mechanisms that are provided so as to form pairs with the respective main bending mechanisms and parallel thereto and that exert a pressing force and a tensile force in the longitudinal direction on the distal end portion at the same positions as or in the vicinity of the respective main linear members; and a switching portion that selectively actuates either the main bending mechanisms or the auxiliary bending mechanisms, which are paired.

BRIEF DESCRIPTION OF DRAWINGS

FIG. 4B is a diagram for explaining the working of the main bending mechanism in FIG. 4A.

FIG. 14A is a configuration diagram showing another modification of the auxiliary bending mechanism.

DESCRIPTION OF EMBODIMENT

A manipulator 1 according to an embodiment of the present invention and a surgical manipulator system 100 provided with the same will be described below with reference to the drawings.

Figure 1:
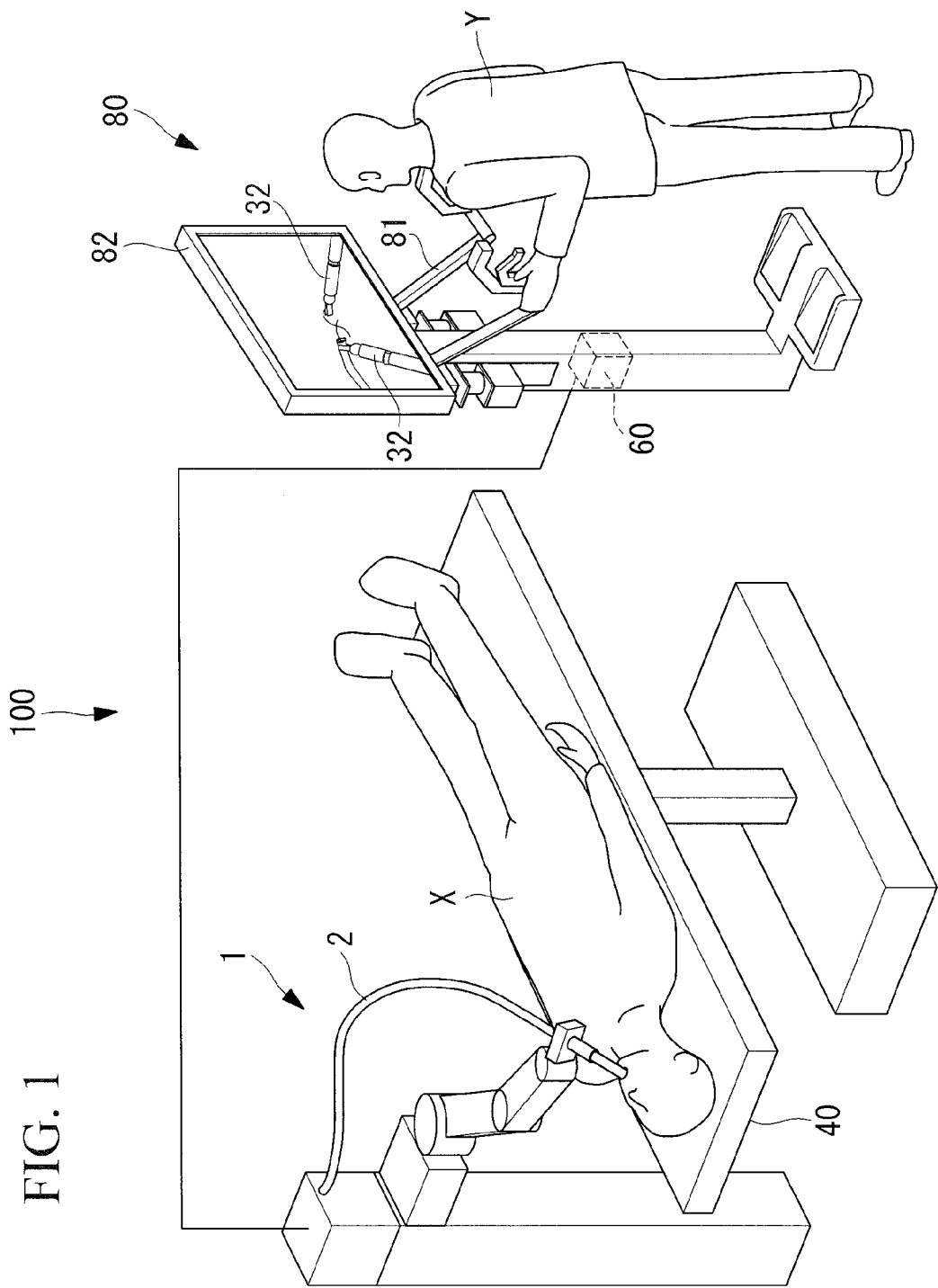
FIG. 1 is an overall configuration diagram of a surgical manipulator system according to an embodiment of the present invention.

FIG. 1 is a diagram showing, in outline, the surgical manipulator system 100 according to this embodiment. As shown in FIG. 1, the surgical manipulator system 100 is provided with the manipulator 1 disposed in the vicinity of a bed 40 on which a patient X is lying, a control device 60 connected to the manipulator 1, and a manipulation device 80 with which manipulation signals for the manipulator 1 are input to the control device 60.

Figure 2:
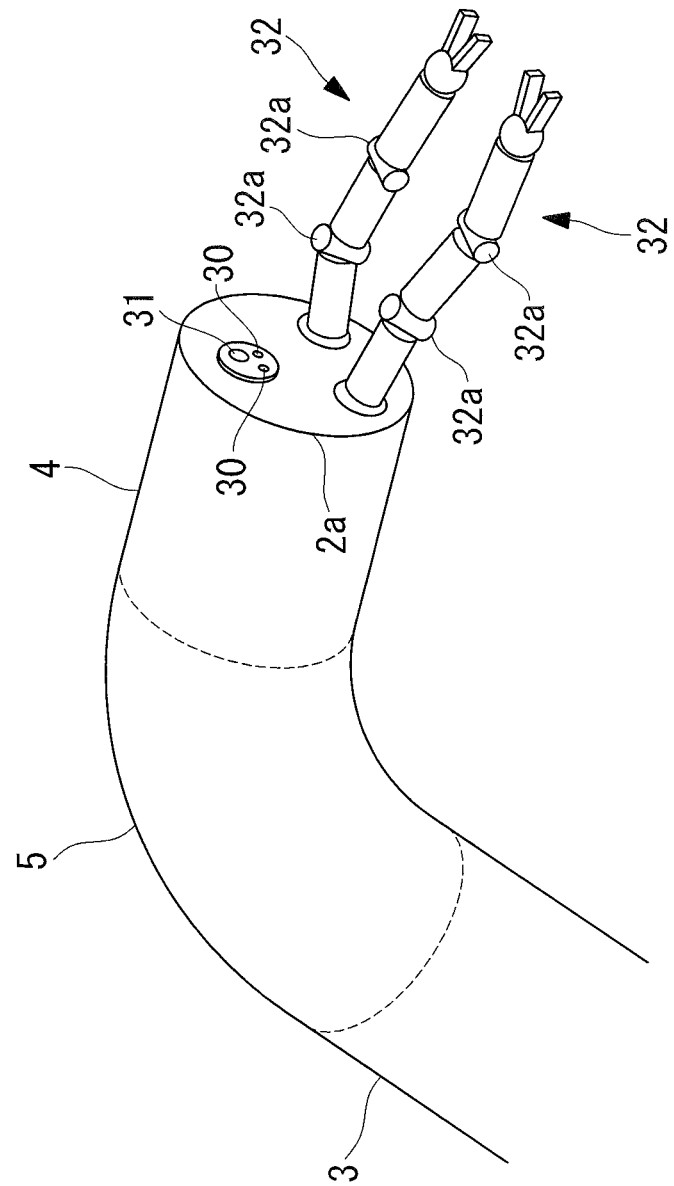
FIG. 2 is a perspective view showing the configuration of a portion at the distal end of a manipulator provided in the surgical manipulator system in FIG. 1.

FIG. 2 shows a portion at the distal end of the manipulator 1 according to this embodiment. As shown in FIG. 2, the manipulator 1 is provided with a light 30 that emits illumination light and a camera 31 that acquires an image of the body interior, which are both provided at a distal-end surface 2a, and a treatment tool 32 that is provided so as to be protrudeable/retractable from the distal-end surface 2a. The treatment tool 32 that protrudes from the distal-end surface 2a is configured so as to be placed in a viewing field of the camera 31. In addition, as will be described later, the manipulator 1 is configured so that the direction in which the distal-end surface 2a points can be changed by bending a bending portion 5 and so that an image-acquisition area of a portion to be operated on in the patient X can be arbitrarily changed.

The manipulation device 80 is provided with an input portion 81, such as a joystick or the like, operated by an operator Y and a display portion 82 on which an image obtained by the camera 31 is displayed.

In response to the inputs from the input portion 81, the control device 60 outputs instruction signals to individual portions of the manipulator 1. In accordance with these instruction signals, the protruding/retracting operation of the treatment tool 32 and the rotational operation of individual joints 32a are controlled, and, in addition, the bending operation of the bending portion 5 is controlled.

The operator Y can treat the inside of the body of the patient X by remotely manipulating the bending portion 5 and the treatment tool 32 of the manipulator 1 via the input portion 81 of the manipulation device 80, while observing the image of the body interior and the treatment tool 32 acquired by the camera 31 on the display portion 82.

Next, the manipulator 1 according to this embodiment will be described in detail.

The manipulator 1 is provided with an elongated inserted portion 2 that is inserted into the body of the patient X, for example, from his/her oral cavity. The inserted portion 2 is provided with an elongated main unit 3, a distal end portion 4 that is disposed at the distal end of the main unit 3, and the bending portion 5 that is disposed between the main unit 3 and the distal end portion 4 to connect them.

The main unit 3 is a portion possessing flexibility which allows it to bend so as to conform to the tissue shape in the body of the patient X.

The distal end portion 4 is a portion in which the light 30, the camera 31, the treatment tool 32, and so forth, described above, are installed and that is rigid and sufficiently small.

Figure 3A:
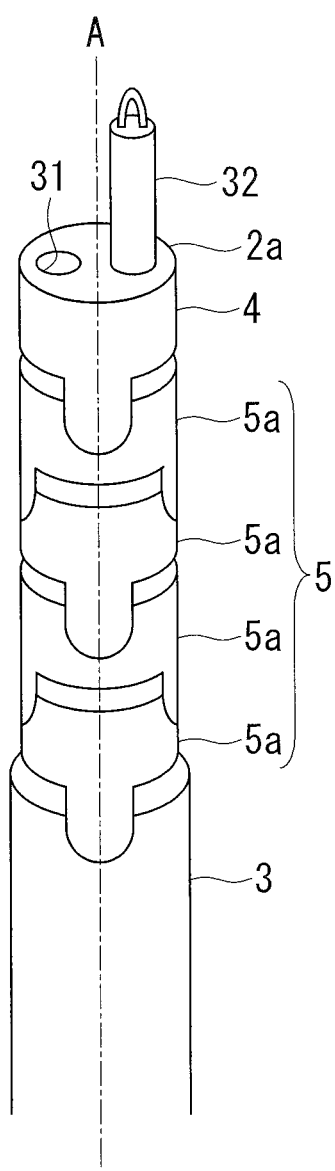
FIG. 3A is a diagram showing, in outline, a bending portion in the straight state.
Figure 3B:
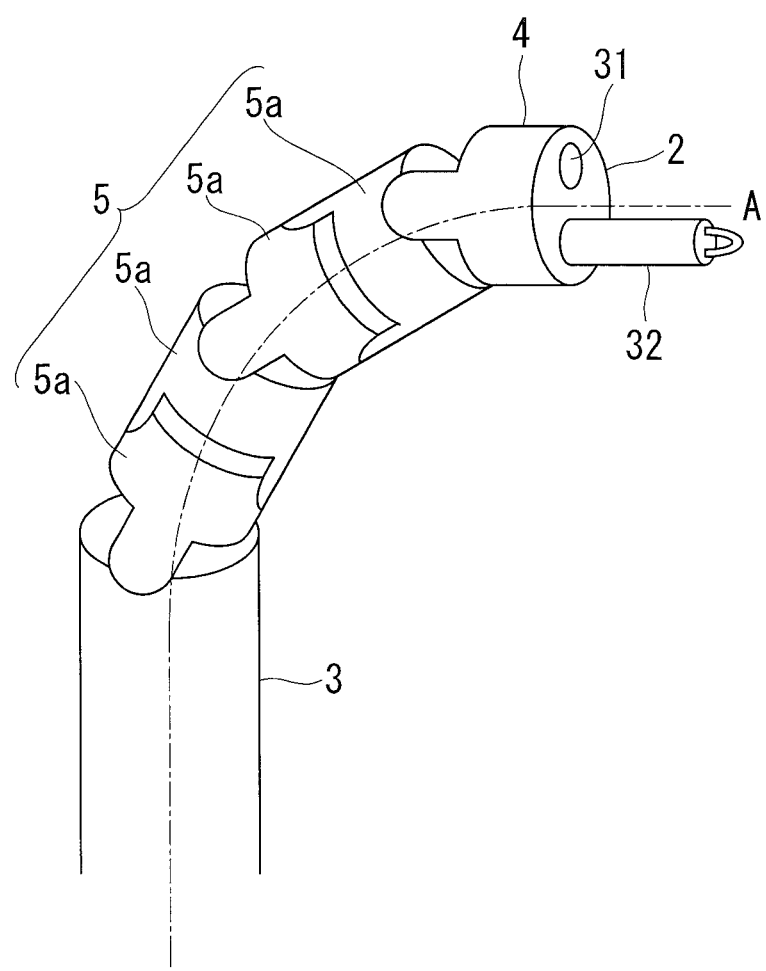
FIG. 3B is a diagram showing, in outline, the bending portion in the bent state.

The bending portion 5 is a portion that is, as described above, bent in a direction that intersects the longitudinal direction of the main unit 3, thus directing the distal-end surface 2a in an arbitrary direction. As shown in FIG. 3A, the bending portion 5 is provided with a plurality of cylindrical joint rings 5a that are arranged along a center axis (hereinafter, also simply referred to as an axis) A of the inserted portion 2. The individual joint rings 5a are coupled with adjacent joint rings 5a so as to be pivotable about two axes that are orthogonal to the axis A. Accordingly, as shown in FIG. 3B, the bending portion 5 is bendable in arbitrary directions. Note that the configuration of the bending portion 5 is not limited to a structure employing the joint rings 5a (bending blocks), and, for example, the bending portion 5 may have a flexing mechanism having a multi-joint structure.

As shown in FIG. 4, as a bending mechanism (main bending mechanism) 6 that controls the bending operation of the bending portion 5, the manipulator 1 is provided with wires (main linear members) 7 whose distal ends are connected to the distal end portion 4 and that extend to the main unit 3 in the axis-A direction and traction mechanisms 8 that are provided in the main unit 3 and that pull the wires 7.

It suffices that the material of the wires 7 be one that possesses rigidity that allows motion at the basal ends to be transmitted to the distal ends, and it is preferable that the material be, for example, metal or plastic. Although the wires 7 are employed as linear members in this embodiment, the form of the linear member is not limited thereto, and it may be, for example, a rod, a tube, a metal coil, or the like.

The traction mechanism 8 is provided with tubular shafts (main shaft members) 9 that are disposed in the axis-A direction, driving mechanisms that are provided at the basal ends of the shafts 9 and that rotate the shafts 9, threaded shafts (motive-power converting members) 10 that are provided coaxially with the shafts 9 and that couple the shafts 9 with the basal ends of the wires 7, and a nut (motive-power converting member) 11 to which the threaded shafts 10 are fastened.

The driving mechanisms are provided with motors 12 that have rotation shafts 12a disposed in the axis-A direction, drive pulleys 131 that are disposed coaxially with the rotation shafts 12a, driven pulleys 132 that are disposed coaxially with the shafts 9 and that are secured to outer circumferential surfaces of the shafts 9, and belts 14 bridging between the drive pulleys 131 and the driven pulleys 132. Between the rotation shafts 12a of the motors 12 and rotation shafts 131a of the drive pulleys 131, joining mechanisms (switching portions) 151 that connect and disconnect them are provided.

When the motors 12 are actuated in a state in which the rotation shafts 12a and the rotation shafts 131a are connected by the joining mechanisms 151, the drive pulleys 131 are rotated together with the rotation shafts 12a, the rotational force of the drive pulleys 131 are transmitted to the driven pulleys 132 and the shafts 9 via the belts 14, and thus, the shafts 9 are rotated about the center axes thereof. When the shafts 9 are rotated in the clockwise direction or in the anticlockwise direction, the threaded shafts 10 are rotated in the clockwise direction or the anticlockwise direction together with the shafts 9.

The nut 11 has four female screws 11a to which four threaded shafts 10 are fastened and commonly holds the four threaded shafts 10. In addition, the nut 11 is secured to a tubular mantle tube of the main unit 3 that accommodates the traction mechanisms 8, and feeds the rotating threaded shafts 10 along the axis-A direction toward the distal end or the basal end with respect to the main unit 3. When the threaded shafts 10 are moved forward toward the distal end, the wires 7 that have been pushed out toward the distal end press the distal end portion 4 toward the distal end, and, when the threaded shafts 10 are moved back toward the basal end, the wires 7 that have been pulled toward the basal end pull the distal end portion 4 toward the basal end.

Figure 4A:
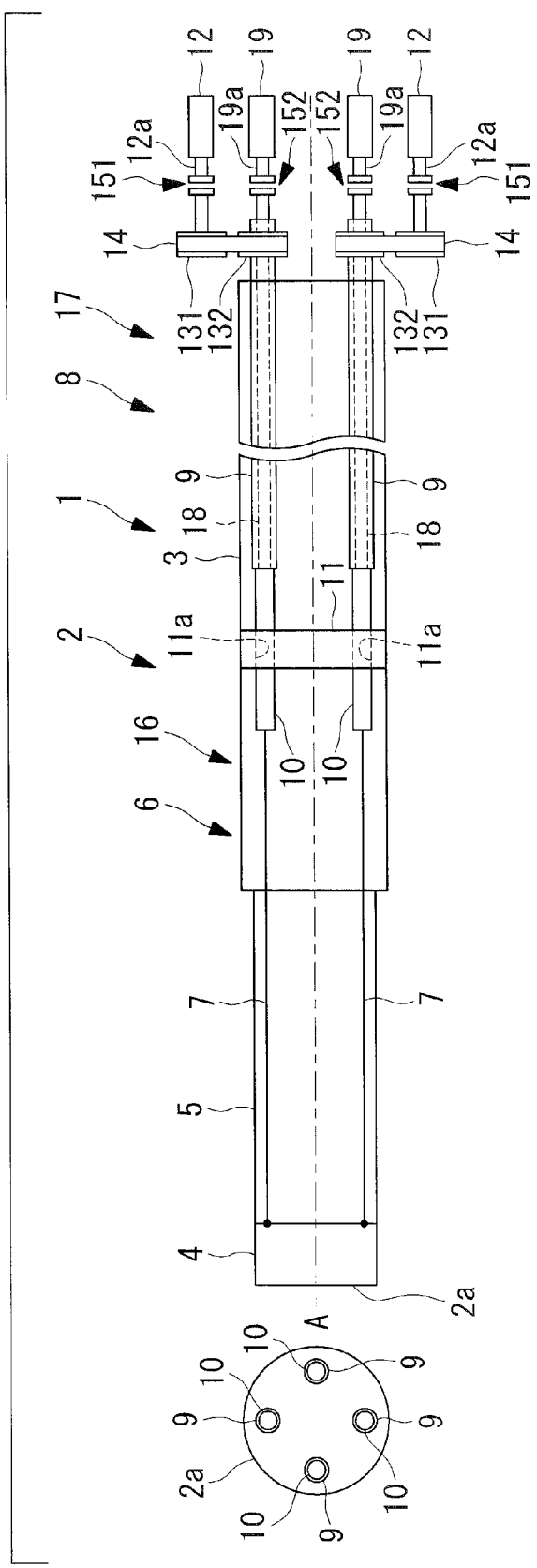
FIG. 4A is a configuration diagram of a main bending mechanism provided in the manipulator.

Here, as shown in the left diagram in FIG. 4A, four sets of the wires 7 and the traction mechanisms 8 are provided on a circumference centered on the axis A with spaces therebetween. In other drawings to which reference is made, only two sets of the wires 7 and the traction mechanisms 8 are shown in order to simplify the drawings. Of the four wires 7, some are pushed and others are pulled, and thus, the bending portion 5 is bent, as shown in FIG. 4B. By adjusting the amounts by which the wires 7 are pushed and pulled at this time, the bending angle of the bending portion 5 is controlled. Note that the bending portion 5 is simplified in the drawings in FIG. 4A and thereafter.

In addition, the manipulator 1 is provided with auxiliary bending mechanisms 16 that are paired with the individual bending mechanisms 6 so as to be disposed parallel thereto. The auxiliary bending mechanisms 16 are provided for the wires 7 so as to be parallel to the traction mechanisms 8 and are provided with, as with the traction mechanisms 8, auxiliary traction mechanisms 17 that manipulate the wires 7 in the axis-A direction.

Specifically, the auxiliary traction mechanisms 17 are provided with auxiliary shafts (auxiliary shaft members) 18 that are disposed coaxially with the shafts 9 of the traction mechanisms 8 and auxiliary motors 19 that are provided at the basal ends of the auxiliary shafts 18. The auxiliary shafts 18 are formed of wires possessing flexibility that allows them to bend so as to conform to the tissue shape in the body while possessing appropriate rigidity for efficiently transmitting the rotational motion at the basal ends to the distal ends, and are accommodated inside the shafts 9. The distal ends of the auxiliary shafts 18 are coupled with the basal ends of the threaded shafts 10 and the basal ends of the auxiliary shafts 18 protrude from the basal ends of the shafts 9.

The auxiliary motors 19 have rotation shafts 19a that are disposed coaxially with the auxiliary shafts 18. Between the auxiliary shafts 18 and the rotation shafts 19a, joining mechanisms (switching portions) 152 that connect and disconnect them are provided. When the auxiliary motors 19 are actuated in a state in which the auxiliary shafts 18 and the rotation shafts 19a are connected by the joining mechanisms 152, the auxiliary shafts 18 are rotated together with the rotation shafts 19a, and, similarly to when the traction mechanisms 8 are actuated, the wires 7 are bent by the movement of the threaded shafts 10 in the axis-A direction.

Here, in a normal state, the auxiliary shafts 18 are disconnected from the auxiliary motors 19 by the joining mechanisms 152, thus being movable in the axis-A direction. Accordingly, the traction mechanisms 8 can be actuated without being blocked by the auxiliary traction mechanisms 17.

Figure 5:
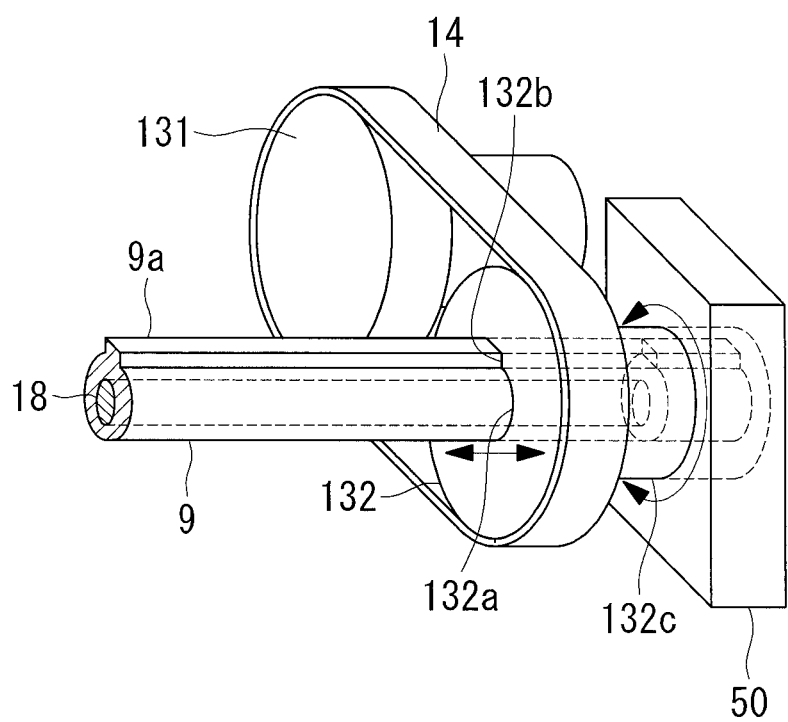
FIG. 5 is a diagram showing the configuration of a portion connecting with a shaft-driven pulley.

FIG. 5 shows the connecting portion between the shaft 9 and the driven pulley 132. A protrusion 9a is formed at a portion in the circumferential direction on the outer circumferential surface of the shaft 9. A hole 132a into which the shaft 9 is inserted in the longitudinal direction in a movable manner is formed in the driven pulley 132, and the hole 132a has a depression 132b to which the protrusion 9a is fitted. The reference sign 50 is a support base that supports a rotation shaft 132c of the pulley 132 in a rotatable manner via a bearing (not shown). By doing so, when the driven pulley 132 is rotated, the shaft 9 is also moved forward or backward in association with the forward or backward movement of the threaded shaft 10 while the shaft 9 is also rotated together with the driven pulley 132.

Next, the operation of the surgical manipulator system 100 provided with the thus-configured manipulator 1 will be described.

In order to treat a portion to be operated on in a patient X by using the surgical manipulator system 100 according to this embodiment, first, the operator Y actuates the manipulator 1 by manipulating the input portion 81, and adjusts the position and attitude of the distal-end surface 2a so as to bring the portion to be operated on into the viewing field of the camera 31 by changing the bending direction and the bending angle of the bending portion 5.

Next, the operator Y manipulates the input portion 81 to make the treatment tool 32 protrude from the distal-end surface 2a, thus moving the treatment tool 32 into the viewing field of the camera 31. The operator Y can treat the portion to be operated on by remotely manipulating the treatment tool 32 via the input portion 81, while observing the positional relationship between the portion to be operated on and the treatment tool 32 in the image displayed on the display portion 82.

Figure 6:
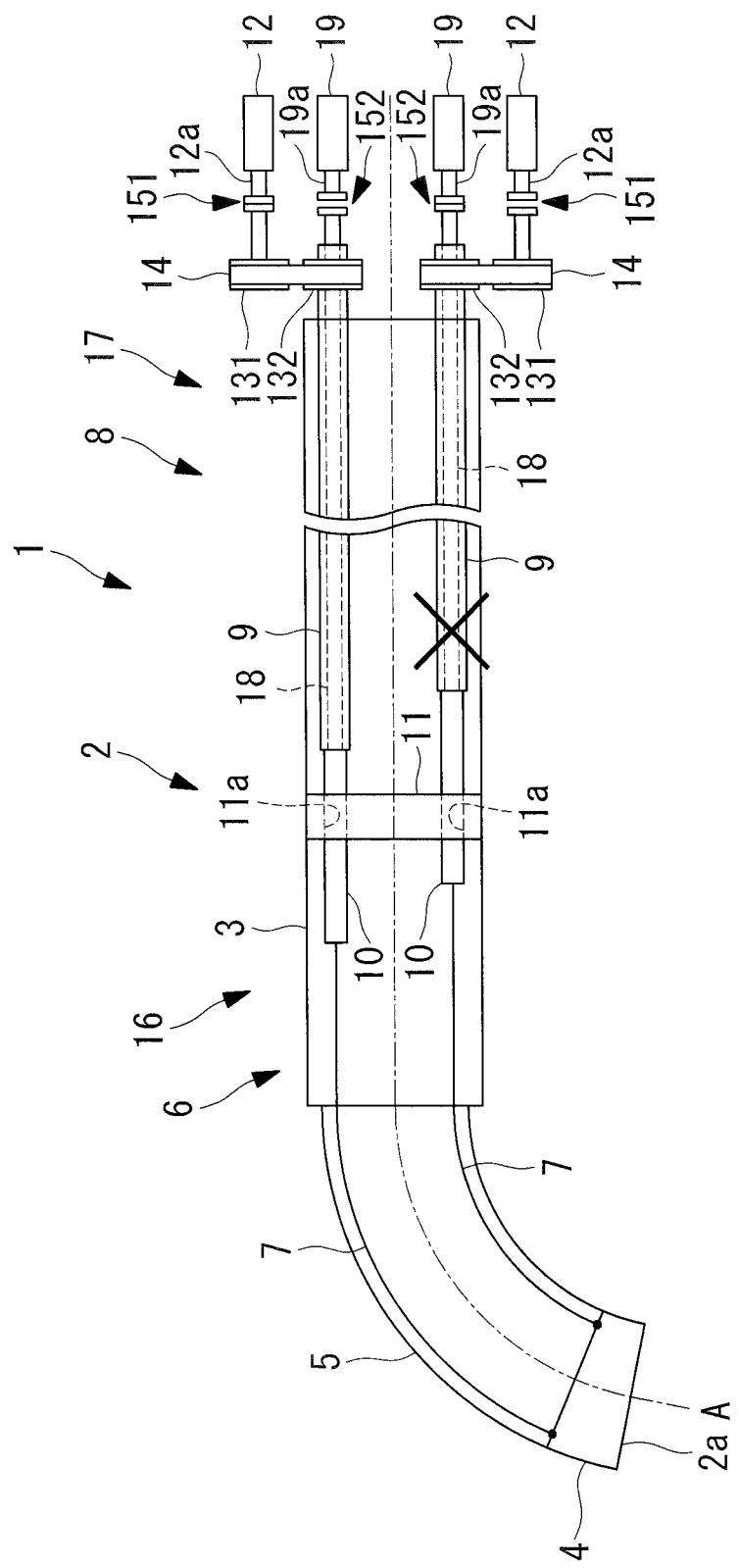
FIG. 6 is a diagram for explaining the operation of a switching portion when a traction mechanism has failed.

Here, as shown in FIG. 6, if the transmission of the motive powers from the motors 12 to the basal ends of the wires 7 stops while the manipulator 1 is being manipulated due to breakage of one of the shafts 9 of the traction mechanisms 8, the bending angle of the bending portion 5 is no longer changed in accordance with the inputs made by the operator Y via the input portion 81, and thus, the viewing field of the camera 31 that is displayed on the display portion 82 is no longer moved normally. Therefore, the operator Y can easily recognize a failure in the traction mechanisms 8.

Here, in the configuration in which the wires 7 are driven by converting relatively large rotational motions of the motors 12 to relatively small linear motions via the threaded shafts 10 and the nut 11, in order to rotationally move the threaded shafts 10 and the shafts 9 by means of the linear motion of the wires 7, it is necessary to linearly move the wires 7 with a sufficiently large force. Specifically, even if a pressing force acts on the distal end portion 4 and the bending portion 5 from tissue in the body, this pressing force is not sufficient to move the wires 7 in the axis-A direction and to deform the bending portion 5, and thus, the bending portion 5 continues to maintain a certain shape without conforming to the tissue shape in the body.

Therefore, the operator Y actuates the two joining mechanisms 151 and 152 after determining the occurrence of a failure in the traction mechanisms 8. Specifically, as shown in FIG. 6, the shaft 9 of the failed traction mechanism 8 is disconnected from the motor 12 by the joining mechanism 151, and the auxiliary shaft 18 of the auxiliary traction mechanism 17 paired with that traction mechanism is connected to the auxiliary motor 19 by the joining mechanism 152. By doing so, the wire 7 that was connected to the failed traction mechanism 8 is restored to a state in which the wire 7 can be manipulated by the auxiliary traction mechanism 17 in a similar manner as before the failure. Therefore, the operator Y can smoothly move and pull out the inserted portion 2 by making it conform to the tissue shape in the body while controlling the bending angle of the bending portion 5 by means of the normal traction mechanisms 8 and the auxiliary traction mechanisms 17.

As above, with this embodiment, in the case in which a traction mechanism 8 fails, by switching that traction mechanism 8 to an auxiliary traction mechanism 17, the bending angle of the bending portion 5 can be restored to a controllable state. Therefore, there is an advantage in that the operator Y can smoothly pull out the manipulator 1 from the body. In addition, by forming a two-layered structure by coaxially disposing the shaft 9 and the auxiliary shaft 18, it is possible to employ a structure having a small diameter in the inserted portion 2.

Note that, in this embodiment, the auxiliary traction mechanism 17 is provided with the auxiliary motor 19 that is separate from the motor 12 of the traction mechanism 8, and the wire 7 is driven by using the auxiliary motor 19 at the time of a failure; however, alternatively, the auxiliary traction mechanism 17 may employ the same motor 12 that is shared with the traction mechanism 8. By doing so, it suffices to include just one motor 12, and it is possible to simplify the apparatus configuration.

Figure 7:
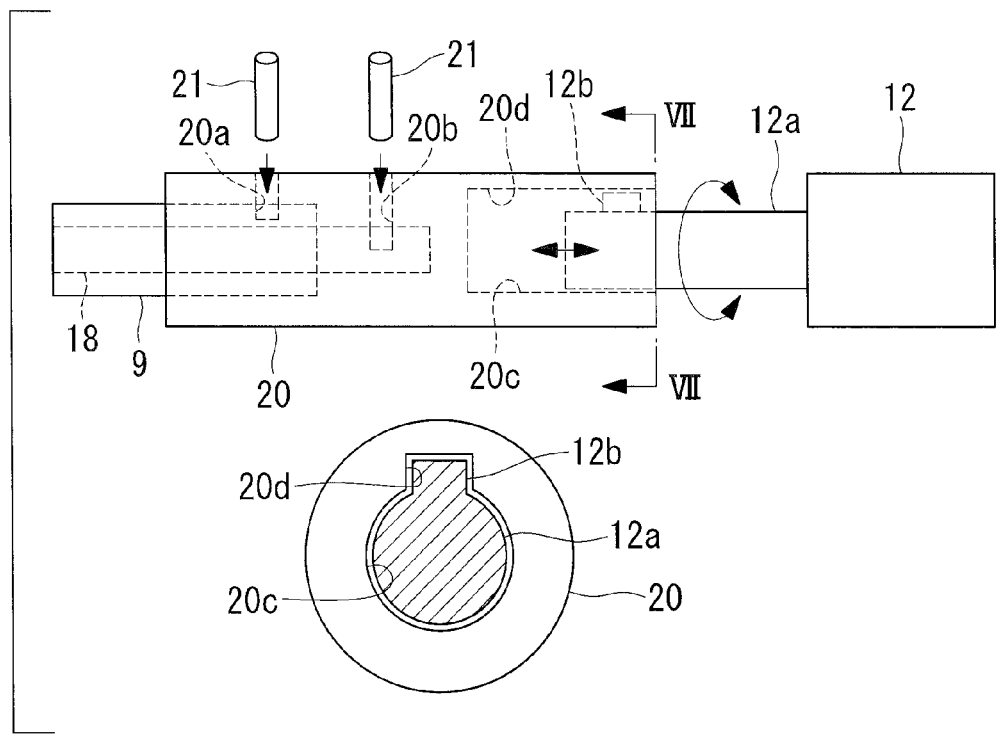
FIG. 7 is a side view (top diagram) showing a modification of the switching portion and a cross-sectional view thereof (bottom diagram) taken along VII-VII.

In this case, by selectively connecting the rotation shaft 12a of the motor 12 to either the shaft 9 or the auxiliary shaft 18, the switching portion selectively actuates either the traction mechanism 8 or the auxiliary traction mechanism 17. For example, as shown in FIG. 7, the switching portion is disposed between the rotation shaft 12a and the shaft 9 and between the rotation shaft 12a and the auxiliary shaft 18, and are provided with an intermediate member 20 secured to the rotation shaft 12a, and a coupling member 21 that couples the intermediate member 20 with the shaft 9 or the auxiliary shaft 18.

The intermediate member 20 is a tubular member in which basal ends of the shaft 9 and the auxiliary shaft 18 are accommodated. The coupling members 21 are pins that are inserted into holes 20a and 20b that communicate among the intermediate member 20, the shaft 9, and the auxiliary shaft 18, and, by inserting the coupling member 21 into one of the holes 20a and 20b, the rotation shaft 12a can be coupled with the shaft 9 or the auxiliary shaft 18 via the intermediate member 20. The holes 20a and 20b may be female screws, and the coupling members 21 may be a male screw. The intermediate member 20 is provided so as to be movable in the longitudinal direction with respect to the rotation shaft 12a in association with the forward or backward movement of the threaded shaft 10. Specifically, the rotation shaft 12a is provided with a protrusion 12b at an outer circumferential surface thereof, a hole 20c is formed at the basal-end surface of the intermediate member 20 in the longitudinal direction, and the hole 20c has a depression 20d that is fitted to the protrusion 12b.

Figure 8:
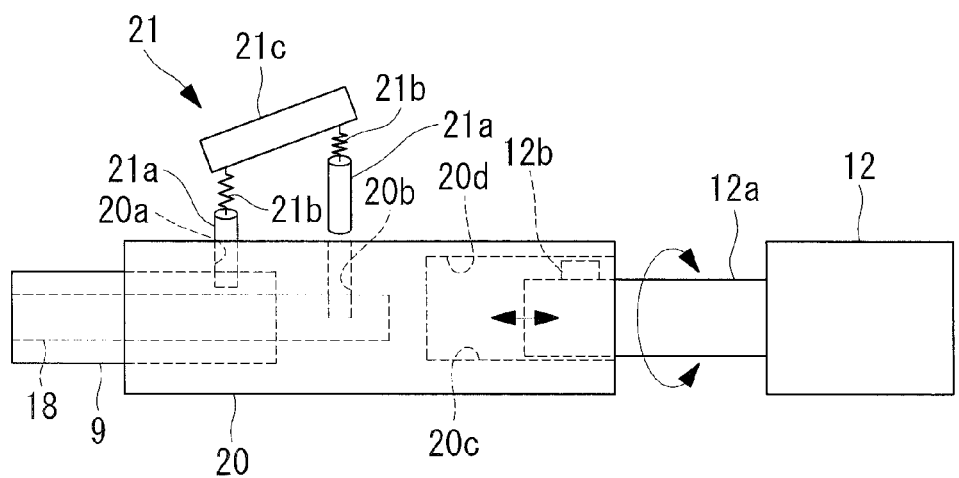
FIG. 8 is a diagram showing another modification of the switching portion.

As shown in FIG. 8, the coupling member 21 may be provided with a switch 21c that is connected to the pins 21a via springs 21b and may be configured so that the pins 21a are inserted into one of the holes 20a and 20b by the actuation of the switch 21c.

Figure 9:
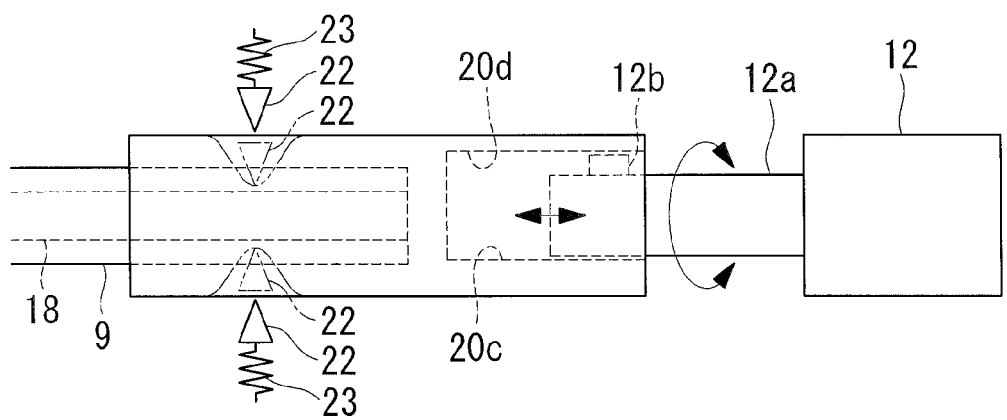
FIG. 9 is a diagram showing yet another modification of the switching portion.

Alternatively, at the time of a failure in the traction mechanism 8, the switching portion may integrally rotate the auxiliary shaft 18 and the shaft 9 by securing the auxiliary shaft 18 to the shaft 9 secured to the rotation shaft 12a of the motor 12. For example, as shown in FIG. 9, the switching portion is provided with a wedge-shaped clamping member 22 that is disposed with the sharp end thereof facing the outer circumferential surface of the shaft 9 and a biasing member 23 that biases the clamping member 22 radially inward of the shaft 9 like a spring. As indicated by two-dot chain lines in the figure, the shaft 9 is secured to the auxiliary shaft 18 by clamping the external surface of the shaft 9 radially inward by means of the clamping member 22.

Figure 10:
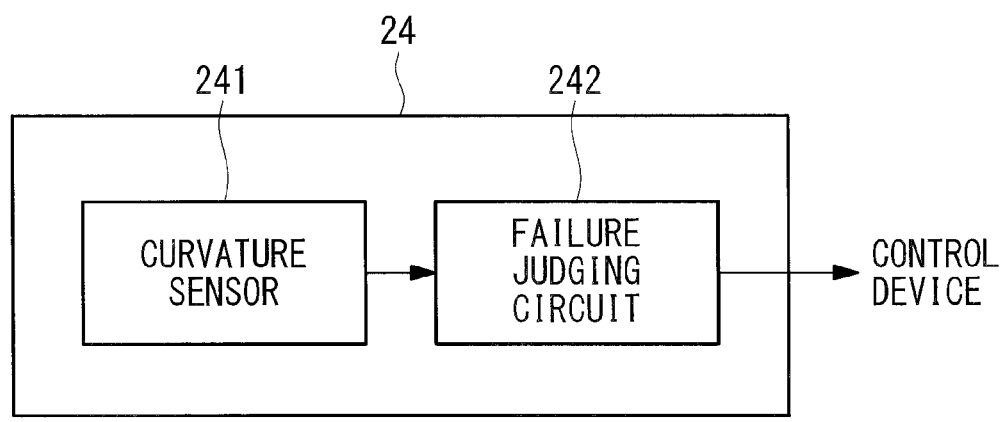
FIG. 10 is a block diagram showing the configuration of a failure detecting portion provided in the manipulator.

In addition, the operator Y determines the occurrence of a failure in the traction mechanism 8 and manually actuates the joining mechanisms 151 and 152 in this embodiment; however, alternatively, as shown in FIG. 10, the manipulator 1 may be provided with a failure detecting portion 24 that detects a failure in the traction mechanism 8. By doing so, it is possible to more reliably detect a failure in the traction mechanism 8, and it is also possible to reduce the burden on the operator Y.

The failure detecting portion 24 is provided with, for example, a curvature sensor 241 that detects the bending angle of the bending portion 5 and a failure judging circuit 242 that compares the bending angle detected by the curvature sensor 241 and a bending angle defined by an instruction signal transmitted from the control device 60 to the motor 12.

The curvature sensor 241 transmits the detected bending angle of the bending portion 5 to the failure judging circuit 242. The failure judging circuit 242 receives the instruction signal that is output from the control device 60 to the motor 12, judges that a failure has occurred in the traction mechanism 8 to which this motor 12 belongs when the difference between the bending angle received from the curvature sensor 241 and the bending angle defined by the instruction signal is greater than a predetermined threshold, and transmits the judgment result to the control device 60.

As the curvature sensor 241, for example, an optical fiber that is disposed in the bending portion 5 in the axis-A direction and that is integrally bent with the bending portion 5 is employed. Notches are formed at multiple positions in the longitudinal direction at the outer circumferential surface of the optical fiber so that light leaks out from the notches in a bent state. The amount of this light leakage is correlated with the bending angle of the optical fiber. Therefore, it is possible to detect the bending angle of the bending portion 5 based on the amount of the light leakage from the optical fiber.

In addition, instead of an optical fiber, a wire sensor or an image sensor may be employed.

The wire sensor is provided with a detection wire that is disposed substantially parallel to the wire 7 of the bending mechanism 6, and detects the bending angle of the bending portion 5 based on the amount of movement of the detection wire in the axis-A direction caused by bending of the bending portion 5.

The image sensor acquires an image of a predetermined marker attached to the treatment tool 32 by using the camera 31, and detects the bending angle of the bending portion 5 based on the angle at which the image of the marker is acquired by analyzing the acquired image.

In addition, the failure detecting portion 24 may detect a failure in the traction mechanism 8 by utilizing a current sensor or a strain sensor instead of the curvature sensor 241.

The current sensor detects current flowing in the motor 12, and the failure judging circuit 242 judges that a failure has occurred in the traction mechanism 8 when the current sensor detects current that is too high or too low relative to current that could normally flow in the motor 12.

The strain sensor measures stress generated at the shaft 9, and the failure judging circuit 242 judges that a failure has occurred in the traction mechanism 8 when the strain sensor has detected stress that is too high or too low relative to the stress that is normally generated at the shaft 9.

As above, in the case in which a failure in the traction mechanism 8 is automatically detected by means of the failure detecting portion 24, the control device 60 may execute switching to the auxiliary traction mechanism 17 of the failed traction mechanism 8 by actuating the joining mechanisms 151 and 152 in response to the judgment result of the failure detecting portion 24.

In addition, when a failure in the traction mechanism 8 is detected by the failure detecting portion 24, the control device 60 may notify the occurrence of the failure to the operator Y.

Notification to the operator Y is performed by, for example, displaying a warning on the display portion 82, lighting a lamp, sounding an alarm, or the like. Instead of these notifications or in addition thereto, the control device 60 may impose restrictions on the operation of the manipulator 1 by the operator Y, for example, by prohibiting control of the manipulator 1 by the operator Y via the input portion 81 or by applying a load to the operation of the input portion 81 by the operator Y, thus slowing down the operation of the manipulator 1.

Next, modifications of the manipulator 1 according to this embodiment described above will be described. In the individual modifications, because the configurations of mainly the auxiliary bending mechanism 16 differ from each other, the configurations of the auxiliary bending mechanism 16 will mainly be described, other common configurations will be assigned the same reference signs, and descriptions thereof will be omitted.

{First Modification}

Figure 11:
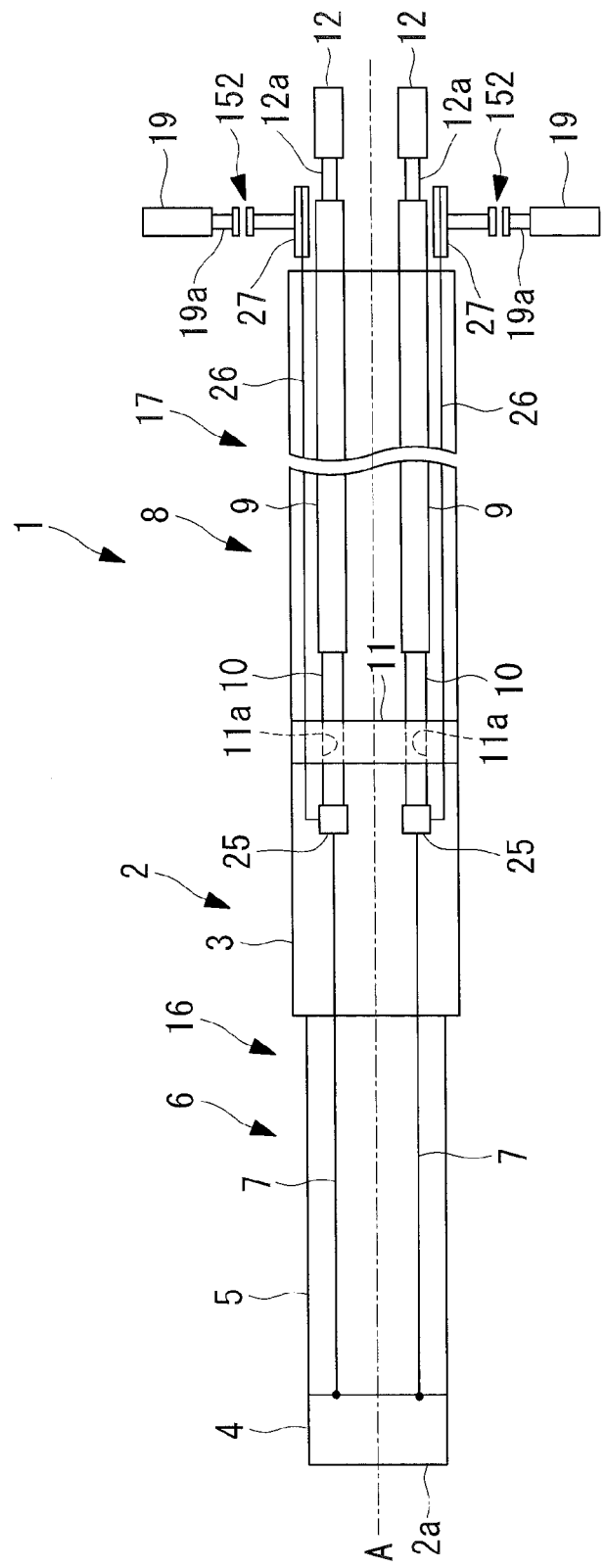
FIG. 11 is a configuration diagram showing a modification of an auxiliary bending mechanism.

In the manipulator 1 according to a first modification of this embodiment, as shown in FIG. 11, the auxiliary traction mechanisms 17 are provided with auxiliary wires (transmitting members) 26 that are connected to intermediate positions of the wires 7 via the connecting members (switching portions) 25 and that extend to the basal end of the main unit 3, auxiliary motors 19 disposed so that the rotation shafts 19a thereof intersect the axis A, and pulleys (auxiliary motive-power generating portions) 27 around which the basal ends of the auxiliary wires 26 are wrapped and that convert the rotational motion of the auxiliary motors 19 to the linear motion in the axis-A direction, and the auxiliary traction mechanisms 17 drive the wires 7 that are shared with the traction mechanisms 8. The basal ends of the shafts 9 are directly coupled with the rotation shafts 12a of the motors 12.

Figure 12A:
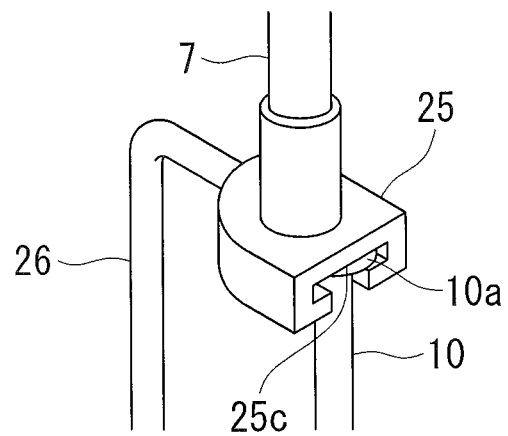
FIG. 12A is a perspective view showing a state in which a wire and a traction mechanism are connected by a connecting member provided in the auxiliary bending mechanism in FIG. 11.
Figure 12B:
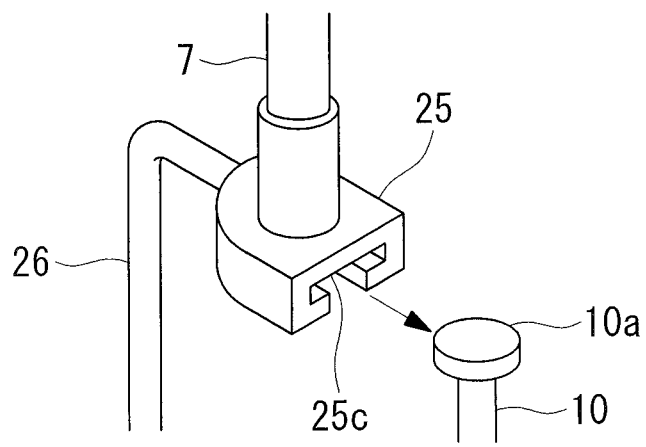
FIG. 12B is a perspective view showing a state in which the wire and the traction mechanism are disconnected by the connecting member provided in the auxiliary bending mechanism in FIG. 11.

FIGS. 12A and 12B show the configuration of the connecting member 25 in detail. As shown in the figures, the threaded shaft 10 has a head portion 10a that protrudes radially outward at the basal end thereof, and the connecting member 25 has a groove 25c to which the head portion 10a is fitted in the radial direction of the main unit 3. As shown in FIG. 12A, the wire 7 is connected to the traction mechanism 8 by fitting the head portion 10 into the groove 25c. On the other hand, as shown in FIG. 12B, the wire 7 is disconnected from the traction mechanism 8 by removing the head portion 10a from the groove 25c. Specifically, the connecting member 25 is tilted when the auxiliary wire 26 is pulled, which causes the head portion 10a to be removed from the opening of the groove 25c in the arrow direction shown in FIG. 12B, and thus, the wire 7 is disconnected from the traction mechanism 8.

Figure 13A:
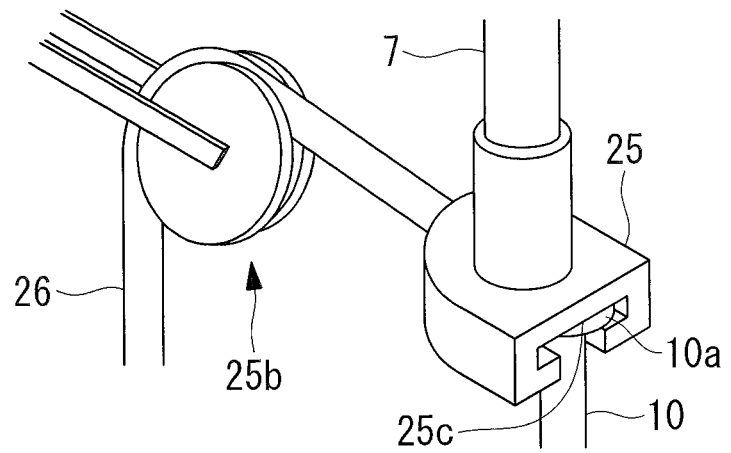
FIG. 13A is a perspective view showing a state in which the wire and the traction mechanism are connected by a modification of the connecting member provided in the auxiliary bending mechanism in FIG. 11.
Figure 13B:
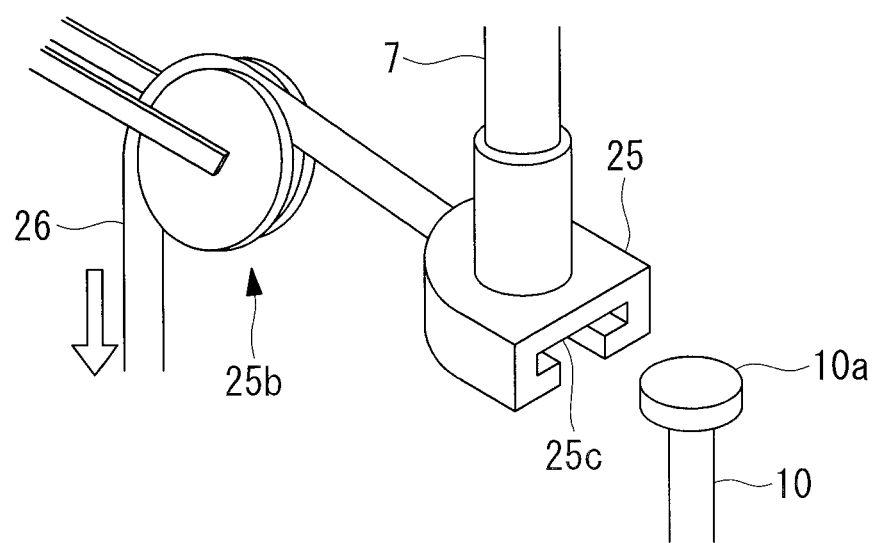
FIG. 13B is a perspective view showing a state in which the wire and the traction mechanism are disconnected by the modification of the connecting member provided in the auxiliary bending mechanism in FIG. 11.

As shown in FIGS. 13A and 13B, the auxiliary wire 26 may be made to run about the pulley 25b. By doing so, it is possible to more easily disconnect the connecting member 25 and the head portion 10a, because the movement of the connecting member 25 is stabilized when the auxiliary wire 26 is pulled.

With the thus-configured manipulator 1 according to this modification, when a failure occurs in a traction mechanism 8, the auxiliary wire 26 is connected to the auxiliary motor 19 by means of the joining mechanism 152, and the wire 7 is disconnected from the traction mechanism 8 by removing the head portion 10a of the threaded shaft 10 from the connecting member 25, thus, making it possible to restore the state in which the bending operation of the bending portion 5 can be controlled by the auxiliary traction mechanism 17. In addition, because members that are accommodated inside the inserted portion 2 all have small diameters, it is possible to employ a small-diameter structure in the inserted portion 2.

{Second Modification}

Figure 14B:
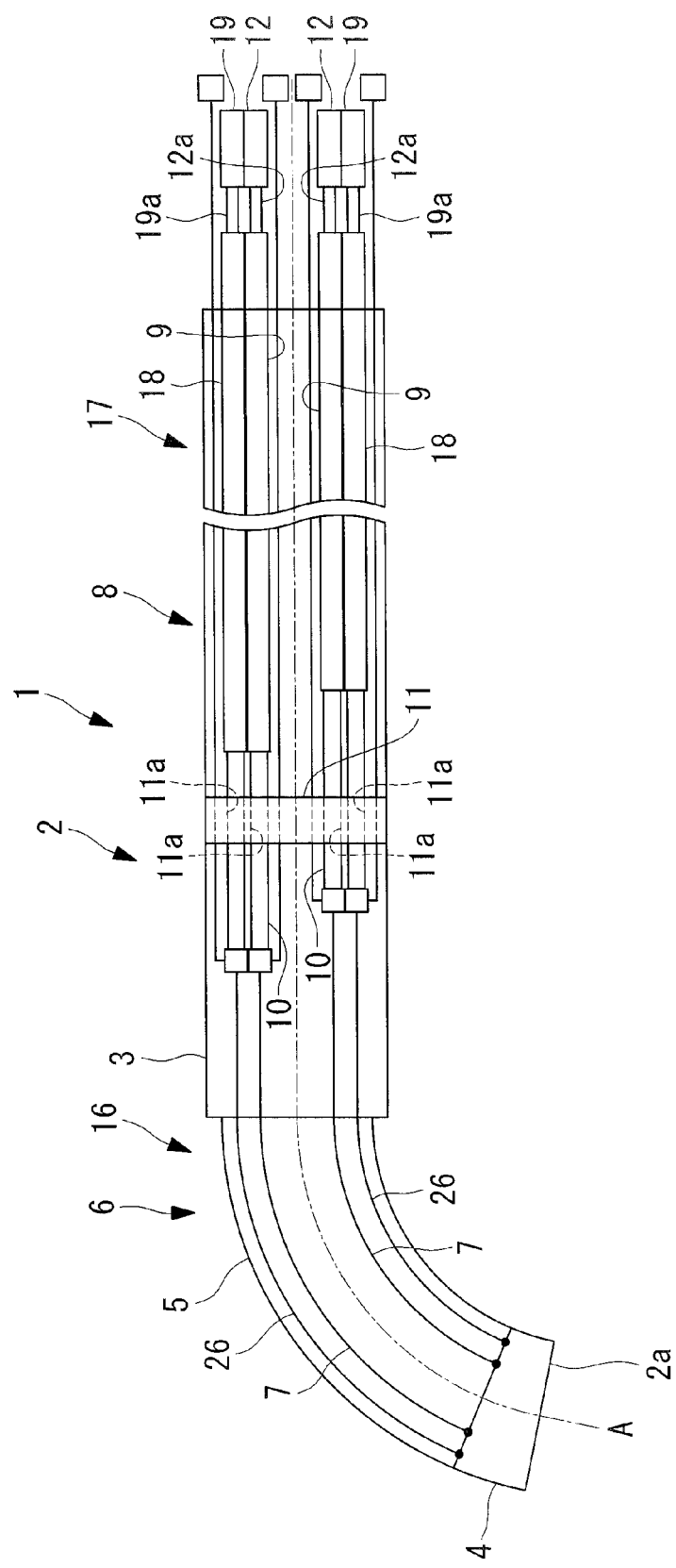
FIG. 14B is a diagram for explaining the operation of the auxiliary bending mechanism in FIG. 14A.

In the manipulator 1 according to a second modification of this embodiment, as shown in FIG. 14A, the auxiliary bending mechanisms 16 are configured in the same manner as the bending mechanisms 6 of the first modification. Specifically, the auxiliary bending mechanisms 16 are provided with the auxiliary wires (auxiliary linear members) 26, the auxiliary threaded shafts (auxiliary motive-power transmitting portions) 28, the auxiliary shafts 18, and the auxiliary motors 19, which are provided parallel to the wires 7, the threaded shafts 10, the shafts 9, and the motors 12. As with the threaded shafts 10, the auxiliary threaded shafts 28 are fastened to female screws 11a that are additionally formed in the nut (auxiliary motive-power transmitting portion) 11. As shown in FIG. 14B, during normal operation, the auxiliary bending mechanisms 16 are actuated together with the bending mechanisms 6.

Figure 15A:
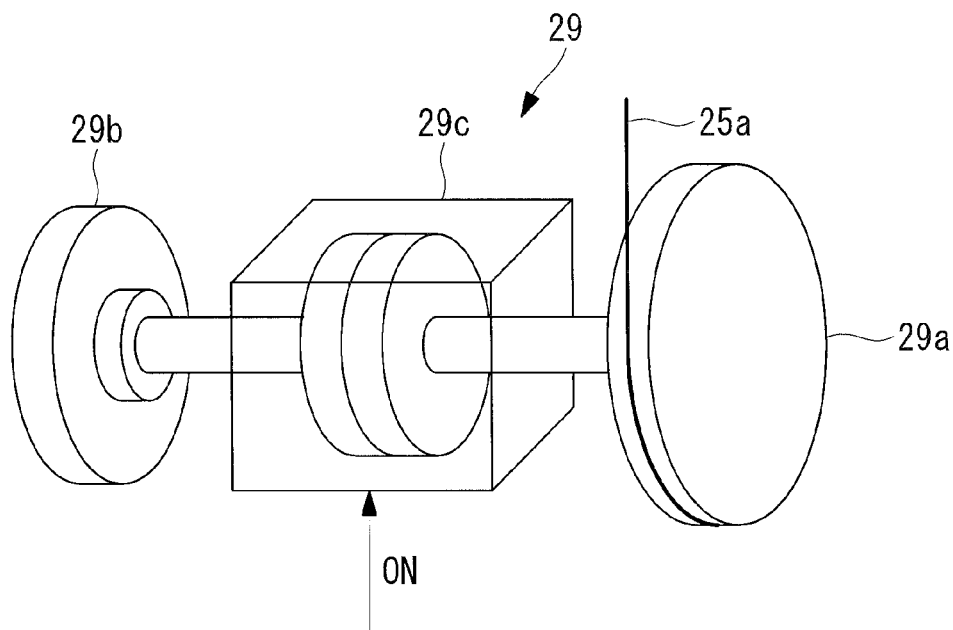
FIG. 15A is a diagram showing the configuration and the operation of a switch control portion in FIG. 14A.
Figure 15B:
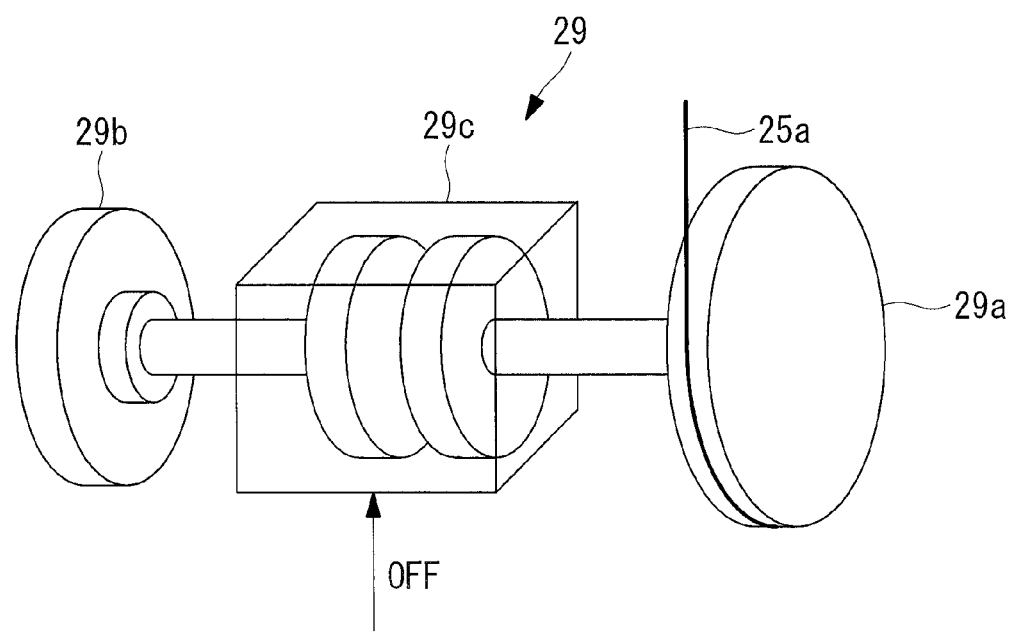
FIG. 15B is a diagram showing the configuration and the operation of the switch control portion in FIG. 14A.

In this modification, the above-described connecting members 25 provided between the wires 7 and the threaded shafts 10 and between the auxiliary wires 26 and the auxiliary threaded shafts 28 and the switch control portions 29 that control connecting and disconnecting of the connecting members 25 with the head portions 10a of the threaded shafts or the head portions of the auxiliary threaded shafts 28 are provided as switching portions. As shown in FIG. 15A, each switch control portion 29 is provided with the electromagnetic clutch 29c that connects or disconnects the pulleys 29a, around which the wire 25a connected to the connecting member 25 is wrapped, and the motor 29b. The wire 25a corresponds to the auxiliary wire 26 in FIGS. 13A and 13B. FIG. 15A shows a state in which the electromagnetic clutch 29c is in the ON state and in which the motor 29b and the pulley 29a are connected, and FIG. 15B shows a state in which the electromagnetic clutch 29c is in the OFF state and in which the motor 29b and the pulley 29a are disconnected.

With the thus-configured manipulator 1 according to this modification, by switching the electromagnetic clutch 29c of the traction mechanism 8 in question from the OFF state to the ON state when a failure occurs in the traction mechanism 8, the pulley 29a is rotated by the motor 29b, and thus, the wire 25a is pulled. By doing so, the failed traction mechanism 8 is separated from the wire 7, and it is possible to control the bending operation of the bending portion 5 by means of the auxiliary traction mechanism 17 paired with the traction mechanism 8 in question. In addition, because members that are accommodated inside the inserted portion 2 all have small diameters, it is possible to employ a small-diameter structure in the inserted portion 2.

{Third Modification}

Figure 16:
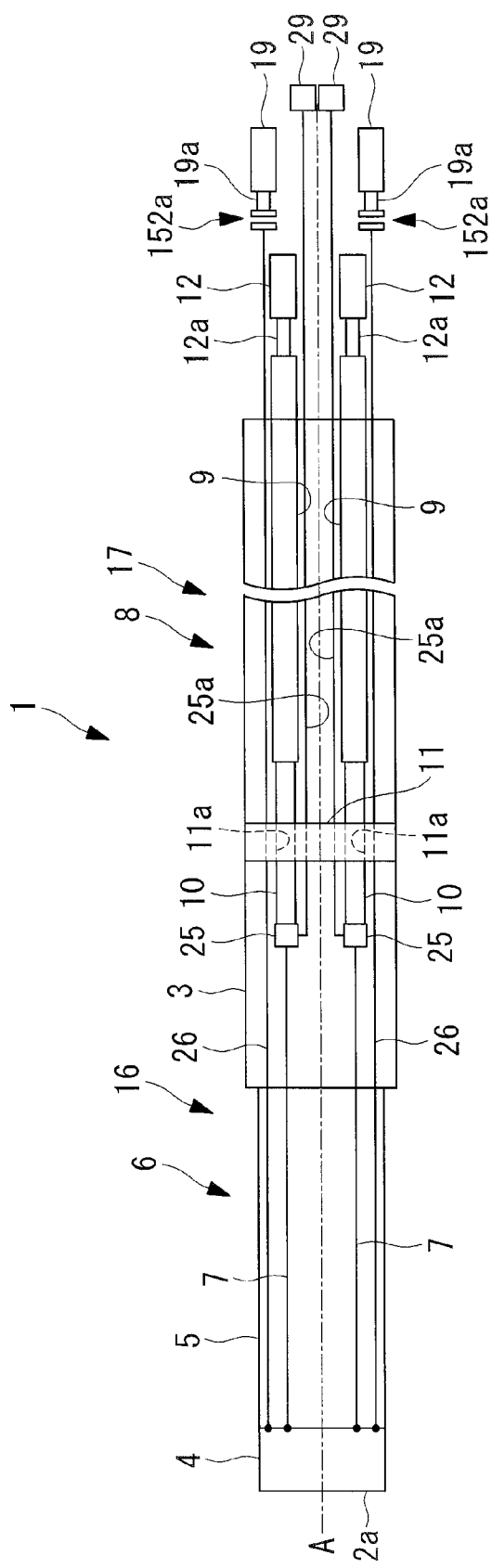
FIG. 16 is a configuration diagram showing yet another modification of the auxiliary bending mechanism.

In the manipulator 1 according to a third modification of this embodiment, as shown in FIG. 16, the auxiliary bending mechanisms 16 are provided with auxiliary wires (auxiliary linear members) 26 whose distal ends are connected to the distal end portion 4 and that extend to the basal end of the main unit 3 and auxiliary motors (auxiliary traction mechanisms) 19. In this modification, the auxiliary motors 19 generate a linear motion in the axis-A direction and transmit this linear motion to the auxiliary wires 26. Between the auxiliary wires 26 and the auxiliary motors 19, the joining mechanisms 152 that connect and disconnect them are provided.

In this modification, as with the second modification, the connecting members 25 and the switch control portions 29 are provided between the wires 7 and the threaded shafts 10 to serve as the switching portions.

With the thus-configured manipulator 1 according to this modification, by switching the electromagnetic clutch 29c of the traction mechanism 8 in question from the OFF state to the ON state when a failure occurs in the traction mechanism 8, the pulley 29a is rotated by the motor 29b, and thus, the wire 25a is pulled. By doing so, the failed traction mechanism 8 is separated from the wire 7. Thus, by connecting the auxiliary wire 26 and the auxiliary motor 19 by means of the joining mechanism 152, it is possible to control the bending operation of the bending portion 5 by means of the auxiliary traction mechanism 17. In addition, because members that are accommodated inside the inserted portion 2 all have small diameters, it is possible to employ a small-diameter structure in the inserted portion 2.

Note that, although the manipulator 1 provided with the mechanism with which the shafts 9 or the intermediate members 20 are moved forward or backward in association with the forward or backward movement of the threaded shafts 10 has been described in this embodiment and the modifications thereof, instead of this mechanism, the shafts 9 may have a length sufficiently greater than the amount of movement of the threaded shafts 10 and may also possess flexibility. By employing such shafts 9 also, it is possible to move the threaded shafts 10 forward or backward.

In addition, although the manipulator 1 provided with the camera 31 and the treatment tool 32 has been described in this embodiment and the modifications thereof, the camera 31 may be omitted as needed.

A following invention can be derived from the above-described embodiment and the modifications thereof.

One aspect of the present invention is a manipulator including an elongated main unit; a distal end portion disposed at a distal end of the main unit; a bending portion that is provided between the main unit and the distal end portion and that is bendable; a plurality of main bending mechanisms that have main linear members that are connected to the distal end portion and that extend to the main unit by passing through the bending portion, main motive-power generating portions that generate motive powers, and main motive-power transmitting portions that are provided in the main unit and that transmit the motive powers generated by the main motive-power generating portions to basal ends of the main linear members in the form of a linear motion of the main unit in the longitudinal direction; a plurality of auxiliary bending mechanisms that are provided so as to form pairs with the respective main bending mechanisms and parallel thereto and that exert a pressing force and a tensile force in the longitudinal direction on the distal end portion at the same positions as or in the vicinity of the respective main linear members; and a switching portion that selectively actuates either the main bending mechanisms or the auxiliary bending mechanisms, which are paired.

With the present invention, the motive power generated by the main motive-power generating portions are transmitted to the basal ends of the main linear members in the form of the linear motion by the main motive-power transmitting portions, and thus, the main linear members are pushed toward the distal end or is pulled toward the basal end. By doing so, the bending portion disposed between the distal end portion and the coupling portion is bent.

In this case, when a failure occurs in the traction mechanism, by actuating the switching portion, it is possible to push and pull the distal end portion by means of the auxiliary traction mechanism instead of the failed traction mechanism. Accordingly, even if the traction mechanism fails, it is possible to smoothly pull out the portion between the distal end portion and the main unit that are inserted into the body. In addition, because it is not necessary to dispose a member having a large diameter, such as a clutch mechanism, in the portion between the distal end portion and the main unit, it is possible to employ a structure having a small diameter.

In the above-described invention, the main motive-power transmitting portions may be provided with main shaft members that are rotated about center axes thereof by the motive powers generated by the main motive-power generating portions and motive-power converting members that convert rotational motions of the main shaft members to linear motions in the longitudinal direction and that are coupled with the basal ends of the main linear members, and the auxiliary bending mechanisms may be provided with auxiliary shaft members that are disposed coaxially with the main shaft members and that are connected with the motive-power converting members and auxiliary motive-power generating portions that rotate the auxiliary shaft members.

By doing so, each main shaft member and auxiliary shaft member, which are connected to the single main linear member so as to be parallel thereto, are coaxially disposed, which makes it possible to control the operation of the bending portion by means of the auxiliary bending mechanisms by using the main linear members shared with the main bending mechanisms, and, in addition, it is possible to effectively reduce the diameter of the main unit.

In the above-described configuration, the main shaft members may be formed of tubular members disposed parallel to the longitudinal direction, and the auxiliary shaft members may be formed of wire-like members that are accommodated inside the main shaft members.

By doing so, it is possible to simplify the configurations of the main shaft members and the auxiliary shaft members.

In the above-described invention, the auxiliary bending mechanisms may be provided with auxiliary linear members that are connected to the distal end portion in the vicinity of the main linear members and that extend toward the basal end and auxiliary traction mechanisms that transmit linear motions in the longitudinal direction to the auxiliary linear members.

By doing so, it is possible to simplify the configuration of the auxiliary bending mechanisms.

In the above-described configuration, the auxiliary traction mechanisms may be provided with auxiliary motive-power generating portions that generate linear motions in the longitudinal direction and transmitting members that are connected to the main linear members and that transmit the linear motions generated by the auxiliary motive-power generating portions to the main linear members.

By doing so, the linear motion generated by the auxiliary motive-power generating portions is transmitted to the main linear members, which are shared with the main bending mechanisms, by the transmitting members. By doing so, it is possible to employ shared components as the main linear members and the auxiliary linear members.

In the above-described configuration, the auxiliary traction mechanisms may be provided with auxiliary motive-power generating portions that are provided parallel to the main motive-power generating portions of the main bending mechanisms and the main motive-power transmitting portions and that generate motive powers and auxiliary motive-power transmitting portions that transmit the motive powers generated by the auxiliary motive-power generating portions to basal ends of the auxiliary linear members in the form of linear motions in the longitudinal direction.

By doing so, it is possible to control the bending operation of the bending portion with the same precision as when using the main bending mechanisms, even after the control is switched to one that uses the auxiliary bending mechanisms.

In the above-described configuration, the auxiliary traction mechanisms may be provided with auxiliary motive-power generating portions that are connected to basal ends of the auxiliary linear members, that generate linear motions in the longitudinal direction, and that transmit the linear motions to the auxiliary linear members.

By doing so, it is possible to simplify the configuration of the auxiliary traction mechanisms.

REFERENCE SIGNS LIST 1 manipulator
2 inserted portion
3 main unit
4 distal end portion
5 bending portion
5a joint ring
6 bending mechanism (main bending mechanism)
7 wire (main linear member)
8 traction mechanism
9 shaft (main shaft member, main motive-power transmitting portion)
10 threaded shaft (motive-power converting member, main motive-power transmitting portion)
11 nut (motive-power converting member, main motive-power transmitting portion, auxiliary motive-power transmitting portion)
12 motor (main motive-power generating portion)
12a rotation shaft
131 drive pulley
131a rotation shaft
132 driven pulley
14 belt
151,152 joining mechanism (switching portion)
16 auxiliary bending mechanism
17 auxiliary traction mechanism
18 auxiliary shaft
19 auxiliary motor (auxiliary motive-power generating portion)
19a rotation shaft
20 intermediate member (switching portion)
21 coupling member (switching portion)
22 clamping member (switching portion)
23 biasing member (switching portion)
24 failure detecting portion
241 curvature sensor
242 failure judging circuit
25 connecting member (switching portion)
25c groove
25b pulley
26 auxiliary wire (transmitting member, auxiliary linear member)
27 pulley (auxiliary motive-power generating portion)
28 auxiliary threaded shaft (auxiliary motive-power transmitting portion)
28 pulley
29 switch control portion
30 light
31 camera
32 treatment tool
32a joint
40 bed
60 control device
80 manipulation device
81 input portion
82 display portion
100 surgical manipulator system
X patient
Y operator

The invention claimed is:
1. A manipulator comprising:
an elongated main unit;
a distal end portion disposed at a distal end of the main unit;
a bending portion that is provided between the main unit and the distal end portion and that is bendable;
a plurality of main bending mechanisms that have main linear members that are connected to the distal end portion and that extend to the main unit by passing through the bending portion, main motive-power generating portions that generate motive powers, and main motive-power transmitting portions that are provided in the main unit and that transmit the motive powers generated by the main motive-power generating portions to the basal ends of the main linear members in the form of a linear motion in the longitudinal direction of the main unit;
a plurality of auxiliary bending mechanisms that are provided so as to form pairs with the respective main bending mechanisms and parallel thereto and that exert a pressing force and a tensile force in the longitudinal direction on the distal end portion at the same positions as or in the vicinity of the respective main linear members; and
a switching portion that selectively actuates either the main bending mechanisms or the auxiliary bending mechanisms, which are paired;
wherein the main motive-power transmitting portions are provided with main shaft members that are rotated about center axes thereof by the motive powers generated by the main motive-power generating portions and motive-power converting members that convert rotational motions of the main shaft members to linear motions in the longitudinal direction and that are coupled with the basal ends of the main linear members, and
the auxiliary bending mechanisms are provided with auxiliary shaft members that are disposed coaxially with the main shaft members and that are connected with the motive-power converting members and auxiliary motive-power generating portions that rotate the auxiliary shaft members.

2. The manipulator according to claim 1,
wherein the main shaft members are formed of tubular members disposed parallel to the longitudinal direction, and
the auxiliary shaft members are formed of wire-like members that are accommodated inside the main shaft members.

3. A manipulator comprising:
an elongated main unit;
a distal end portion disposed at a distal end of the main unit;
a bending portion that is provided between the main unit and the distal end portion and that is bendable;
a plurality of main bending mechanisms that have main linear members that are connected to the distal end portion and that extend to the main unit by passing through the bending portion, main motive-power generating portions that generate motive powers, and main motive-power transmitting portions that are provided in the main unit and that transmit the motive powers generated by the main motive-power generating portions to the basal ends of the main linear members in the form of a linear motion in the longitudinal direction of the main unit;
a plurality of auxiliary bending mechanisms that are provided so as to form pairs with the respective main bending mechanisms and parallel thereto and that exert a pressing force and a tensile force in the longitudinal direction on the distal end portion at the same positions as or in the vicinity of the respective main linear members; and
a switching portion that selectively actuates either the main bending mechanisms or the auxiliary bending mechanisms, which are paired;
wherein the auxiliary bending mechanisms are provided with auxiliary linear members that are connected to the distal end portion in the vicinity of the main linear members and that extend toward the basal end and auxiliary traction mechanisms that transmit linear motions in the longitudinal direction to the auxiliary linear members.

4. The manipulator according to claim 3, wherein the auxiliary traction mechanisms are provided with auxiliary motive-power generating portions that generate linear motions in the longitudinal direction and transmitting members that are connected to the main linear members and that transmit the linear motions generated by the auxiliary motive-power generating portions to the main linear members.

5. The manipulator according to claim 3, wherein the auxiliary traction mechanisms are provided with auxiliary motive-power generating portions that generate motive powers and auxiliary motive-power transmitting portions that transmit the motive powers generated by the auxiliary motive-power generating portions to basal ends of the auxiliary linear members in the form of linear motions in the longitudinal direction, the auxiliary motive-power generating portions and the auxiliary motive-power transmitting portions being respectively provided parallel to the main motive-power generating portions and the main motive-power transmitting portions of the main bending mechanisms.

6. The manipulator according to claim 3, wherein the auxiliary traction mechanisms are provided with auxiliary motive-power generating portions that are connected to basal ends of the auxiliary linear members, that generate linear motions in the longitudinal direction, and that transmit the linear motions to the auxiliary linear members.

* * * * *